United States Patent
Kumar et al.

(10) Patent No.: US 7,179,633 B2
(45) Date of Patent: Feb. 20, 2007

(54) BIOLOGICAL NEUTRALIZATION OF HIGHLY ALKALINE TEXTILE INDUSTRIAL WASTEWATER

(75) Inventors: Rita Kumar, Delhi (IN); Anil Kumar, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/032,697

(22) Filed: Dec. 29, 2004

(65) Prior Publication Data

US 2006/0141605 A1    Jun. 29, 2006

(51) Int. Cl.
C02F 3/34 (2006.01)
C12N 1/02 (2006.01)
C12N 1/12 (2006.01)
C12N 1/20 (2006.01)

(52) U.S. Cl. .................. 435/252.1; 435/261; 435/262; 435/822

(58) Field of Classification Search ...................... None
See application file for complete search history.

(56) References Cited

U.S. PATENT DOCUMENTS

2002/0064864 A1    5/2002    Kumar et al.
2004/0140448 A1    7/2004    Hsiao et al.

OTHER PUBLICATIONS

Sani, R.K., et al. "Decolorization of Triphenylmethane Dyes and Textile and Dye-Stuff Effluent by Kurthia Sp." *Enzyme and Microbial Technology* (1999) vol. 24, pp. 433-437 XP-002347455.

*Primary Examiner*—Michael Wityshyn
*Assistant Examiner*—Deborah K. Ware
(74) *Attorney, Agent, or Firm*—Ladas and Parry LLP

(57) ABSTRACT

The present invention provides a novel process of neutralizing textile industrial wastewater by a bacterial strain isolated in India. The isolated bacterial strain is capable to bring down the pH of wastewater from 12.00 to 7.00 units within two hours. The neutralization of alkaline textile industrial wastewater by such biotechnological process is highly effective and economical as compared to conventional neutralization by chemical means. This biotechnological process may find wide commercial application in textile industries emanating alkaline wastewater.

39 Claims, No Drawings

BIOLOGICAL NEUTRALIZATION OF HIGHLY ALKALINE TEXTILE INDUSTRIAL WASTEWATER

FIELD OF THE INVENTION

The present invention relates to a bacterial isolate, *Kurthia* sp, (MTCC 5181) deposited at IMTECH, Sector 39A, Chandigarh, India recognized by Budapest Treaty. More particularly, the present invention relates to a process for preparing a bacterial isolate *Kurthia* sp, (MTCC 5181) useful in neutralization of alkaline waste water (pH-12.00 to 11.5) of textile industry and deposited at a recognized International Depository at IMTECH, Sector 39A, Chandigarh, India under the Budapest Treaty. The present invention also relates to a process for the neutralization of highly alkaline textile industrial wastewater using the bacterial isolate of the invention.

BACKGROUND AND PRIOR ART

Stringent laws and frequent checks by authorities reflect growing environmental concerns. Thus, for instance, the pH of wastewater of industries such as textiles can deviate only minimally from the neutral point when discharged into a receiving watercourse or sewerage system.

Various chemicals are available to neutralize the high alkaline textile industrial wastewater depending upon the application. In most cases, Sulfuric Acid ($H_2SO_4$) is used. The end user must consider the concentration to be used, must carefully analyze all the chemistries involved, must review manufacturers' warnings and instructions, and must consider common safety measures for hazardous liquids.

The process of treating wastewaters with chemicals comprises use of either acids or bases or substances capable of forming them on addition to wastewater. Various chemicals are available for industrial neutralization depending upon the application and whether neutralization of an acidic or basic solution is being carried out.

The most commonly used neutralization chemicals for acid or base neutralization are 98% Sulfuric acid and 50% Sodium hydroxide. In many cases these are very good choices. However, there are many considerations when selecting chemicals and these may not always be the best selection. The selection of the chemicals used for the neutralization of an acid or base is almost as important as the design of the neutralization system. Some of the major points to consider in the selection of chemicals are listed below:

Health and Safety
Cost and Convenience
Physical Properties of neutralizing chemicals
Storage Environment An explanation of chemical selection criteria is as follows:

Health and Safety: Mixing of chemicals can lead to extreme hazardous/noxious reactions. For example, addition of an acid to cyanide bearing solution results in release of deadly HCN gas. Cost and Convenience: Acids and bases work in most applications. Sulfuric acid ($H_2SO_4$), for example, is less costly and more potent than nitric acid. Concentration is also an important consideration in cost assessment. $H_2SO_4$ for example, can be purchased in concentrations ranging from near 0 to 98%. Higher concentrations are generally less expensive.

Physical Properties: The physical properties of the selected reagent must be considered carefully. 50% Sodium hydroxide (NaOH), for example, begins to freeze at temperatures below 60° F. Decreasing the concentration to 25% eliminates this concern altogether. Hydrochloric acid (HCl), for example, gasses out severely and is highly corrosive and will attack all metallic objects. Therefore, if HCl is used it must be properly vented or used outdoors where the gasses can easily dissipate.

Storage Environment: Storage issues such as the types of tanks and secondary containment available, familiarity of operators in handling hazardous chemicals, the dangers of refilling storage containers or procedures for transferring from bulk containers are of concern.

The most commonly used neutralizing chemicals are listed below:

Acids: Sulfuric Acid, Hydrochloric Acid, Nitric Acid, Phosphoric Acid and Carbon Dioxide which forms Carbonic Acid in water Bases: Sodium Hydroxide (Caustic Soda), Calcium Hydroxide, Calcium Carbonate (Lime or Limestone), Ammonium Hydroxide Neutralization with Acids Sulfuric Acid is the most widely used and produced chemical in the world. Available in concentrations ranging from 0% to 98%, sulfuric acid is most economical of all and used universally for neutralization reactions. It is easier and safer to use than HCl or $HNO_3$ and is more potent than all of the other acids except for phosphoric acid. Sulfuric acid is typically used in concentrations ranging from 25% to 96%. However, 30% to 50% concentrations of sulfuric acid are generally recommended.

Hydrochloric Acid (HCl), also known as muriatic acid, is the second most commonly used acid in industry, sulfuric acid being the primary choice since it is more effective and relatively inexpensive. At a maximum available concentration of 37%, HCl is about ⅓ as potent as sulfuric acid, thus making it relatively more expensive to use. Depending on temperature and agitation, HCl at concentrations above 10% evolves hydrogen chloride vapors which combine with the water vapors present in the air. The gas thus formed, is highly corrosive and attacks all metallic objects including building structures, sprinkler heads, copper wiring, stainless steel, etc. Therefore, it must be properly vented or used outdoors where the gasses can easily dissipate.

Nitric Acid ($HNO_3$) though a widely used chemical in many industries it does not enjoy the popularity of hydrochloric or sulfuric acid, as it is more expensive to use than either of them. Nitric acid evolves noxious gas which on combines with water vapors present in the air. The gas is highly corrosive and attacks all metallic objects including building structures, sprinkler heads, copper wiring, stainless steel, etc. Therefore, it must be properly vented or used outdoors where the gasses can easily dissipate.

Phosphoric Acid ($H_3PO_4$), very widely used in the production of agricultural fertilizers and detergent products it is a relatively inexpensive acid. However it still does not compete well with sulfuric and hydrochloric acid as it is a weak acid and does not fully disassociate in water at normal concentrations. This renders it safer to use compared to sulfuric or hydrochloric acid and the evolution of gasses is rare. It tends to buffer neutralization reactions and this makes for a slower reaction that is easier to control. Due to its cost (as compared to sulfuric acid) and availability, phosphoric acid is not commonly used in neutralization system.

Carbon Dioxide ($CO_2$), the third most concentrated gas found in earth's atmosphere, $CO_2$ is itself not an acid. It forms carbonic acid ($H_2CO_3$) when dissolved in water; and it is this carbonic acid that brings about the neutralization of alkalinity in solution. The most appealing feature of $CO_2$ is that it will not lower the pH of water below 7.0 for all practical purposes. Additionally $CO_2$ is non corrosive. However as it is heavier than air asphyxiation is a hazard. Carbon dioxide is difficult to use and its use is limited because the gas must be dissolved into solution to be used. This requires the use of a carbonator, or some method to dissolve the gas into solution. Significant out-gassing also occurs, which does not hold a problem unless the process also requires the settling of solids. In cement pouring operations large amounts of alkaline wastewaters are generated. It is an excellent choice for such applications as the site is temporary, the gas is nonhazardous, can be used in-line assuming retention and mixing is considered and is self-buffering so regardless of dosage it will not lower the pH below 7.5-7.0.

Alkaliphiles

Several microorganisms exhibit more than one pH optimum for growth depending on growth conditions, particularly nutrients, metal ions, and temperature. The term "alkaliphile" is used for microorganisms that grow optimally or very well at pH values above 9. The first paper concerning an alkaline enzyme of alkaliphilic microorganisms was published in 1971 (Horikoshi, K. (1971) Production of alkaline enzymes by alkalophilic microorganisms. Part 1. Alkaline protease produced by Bacillus No, 221. Agric. Biol. Chem. 36, 1407–1414). Over the past two decades, our studies have focused on the enzymology, physiology, ecology, taxonomy, molecular biology and genetics of alkaliphilic microorganisms. Industrial applications of these microorganisms have also been investigated extensively and some enzymes, such as alkaline proteases, alkaline amylases and alkaline cellulases, have been put to use on an industrial scale (Horikoshi, K. and Akiba, T. (1982) Alkalophilic Microorganisms: A New Microbial World. Springer-Verlag, Heidelberg, Tokyo, Horikoshi, K. (1991) Microorganisms in Alkaline Environments, Kodansha-VCH, Tokyo, Weinheim, N.Y., Cambridge, Basel).

Subsequently, many microbiologists have published numerous papers on alkaliphilic microorganisms in various fields. Cell surface of alkaliphiles can maintain the intracellular pH values neutral in alkaline environments of pH 10–13. In 1995, using alkaliphilic Bacillus C-125 mutants that are alkaline sensitive developed new host vector systems, and genes responsible for alkaliphily have been investigated (Kudo, T., Hino, M., Kitada, M. and Horikoshi, K. (1990) DNA sequences required for the alkalophily of Bacillus sp. strain C-125 are located close together on its chromosomal DNA. J. Bacteriol. 172, 7282–7283, Seto, Y., Hashimoto, M., Usami, R., Hamamoto, T., Kudo, T. and Horikoshi, K. (1995) Characterization of a mutation responsible for an alkali-sensitive mutant, 18224, of alkaliphilic Bacillus sp. strain C-125. Biosei. Biotechnol. Biochem. 59, 1364–1366).

Although alkaliphiles have been used for a number of industrial applications, there is no research publication regarding neutralization of textile industrial wastewater using them. U.S. patent application Ser. No. 09/160422, (1998) discloses a biological neutralization process by using a mixture of bacteria in the presence of sugars.

OBJECTS OF THE INVENTION

The main object of the present invention is to provide a bacterial isolate, Kurthia sp, (MTCC 5181) deposited at International Depository at IMTECH, Sector 39A, Chandigarh, India recognized by Budapest Treaty.

Another object of the present invention is to provide a process of preparing the bacterial isolate bacterium Kurthia sp, (MTCC 5181) deposited at International Depository at IMTECH Sector 39A, Chandigarh, India recognized by Budapest Treaty.

Still another object of the present invention is to isolate a bacterium, Kurthia sp, (MTCC 5181) deposited at International Depository at IMTECH, Sector 39A, Chandigarh, India recognized by Budapest Treaty which is capable to neutralize the highly alkaline waste water of textile industry.

SUMMARY OF THE INVENTION

The present invention provides a bacterial isolate, Kurthia sp, (MTCC 5181) deposited at International Depository at IMTECH, Sector 39A, Chandigarh, India recognized by Budapest Treaty from textile industrial wastewater. This bacterial strain is capable to bring down the pH of wastewater from 12.00 to 7.00 units within two hours. The neutralization of alkaline textile industrial wastewater by such biotechnological process is highly effective and economical as compared to conventional neutralization by chemical means.

In one embodiment of the invention, the bacterial isolate is capable of growth in a medium of pH range of 10.00–12.00.

In another embodiment of the invention, the bacterial isolate is capable of lowering the pH (12.0 to 11.5) of textile industrial wastewater to neutral pH (7.5 to 7.00) within a short period (about two hour).

In another embodiment of the invention, the bacterial pellet is used to neutralize high pH (12.0 to 11.5) of textile industrial wastewater to neutral pH (7.5 to 7.0) in ratio ranging from 1:5 to 1:10.

In another embodiment of the invention, the bacterial isolate is isolated from soil accumulated in a pipe of an effluent treatment plant of textile industry located in Chandigarh, India, through which alkaline wastewater has been passed over a period of long time.

In another embodiment of the invention, the bacterial isolate Kurthia sp is Gram-Positive, motile, catalase positive, and capable of reducing nitrate and hydrolyzing starch.

The present invention also provides a process of preparing a bacterial isolate of bacterium Kurthia sp, (MTCC 5181) useful in neutralization of alkaline waste water (pH-12.00 to 11.5) of textile industry and deposited at International Depository at IMTECH, Sector 39A, Chandigarh, India recognized by Budapest Treaty, the process comprising:

(a) enriching soil contaminated with bacteria by providing a soil extract in basal carbonate medium for a period of 72–96 hours at 100–120 rpm at 35–37° C. in ratio ranges between 1:1–1:2;

(b) culturing the bacteria by using the basal carbonate medium at pH 1.5–12.00 and at 35–37° C. for 8–10 hours;

(c) Isolating the said bacteria by centrifuging the culture obtained from step (b) after attaining the heavy growth (O.D. 1.5–2.0) to obtain a pellet of bacterial cell;

(d) dissolving the pellet obtained from step (c) in phosphate buffer;

(e) neutralizing alkaline waste water (pH-12.00 to 11.5) of textile industry by adding the bacterial pellet obtained from step (d) in wastewater.

In an embodiment of the invention, contaminated soil is obtained from a pipe of an effluent treatment plant of textile industry located in Chandigarh, India.

In another embodiment of the invention, enrichment of the soil from said site is done by taking 5–7 g of fresh soil in an autoclaved flask containing 100–110 ml soil extract, 50 µl Candid B (anti-fungal) and basal carbonate medium.

In another embodiment of the invention, the soil extract is prepared by centrifuging the sterilized soil mixture at about 4000 rpm for about 20 min.

In another embodiment of the invention, the sterilized soil mixture is prepared by dissolving the dried soil in distilled water in ratio about 1:3 and autoclaved it at about 15 psi for about one hour.

In another embodiment of the invention, the basal carbonate medium contains glucose, bacto-peptone, yeast extract, $K_2HPO_4.3H_2O$, $MgSO_4.7H_2O$ and sodium carbonate in ratio about 1:0.5:0.5:0.13:0.02:10 by W/V.

In another embodiment of the invention, a mixture of soil extract and basal carbonate medium is used to entrap the maximum bacterial flora of the site.

In another embodiment of the invention, the ratio between the soil extract and the basal carbonate medium is in the range of 1:1–1:2.

In another embodiment of the invention, isolated bacterial isolates are cultured under defined conditions such as media, temperature, pH, and carbon source.

In another embodiment of the invention, all bacterial isolates (total three) are checked for their neutralizing capability to lower pH of textile wastewater in a short period of time.

In another embodiment of the invention, decrease in pH is monitored by pH meter.

In another embodiment of the invention, a bacterium is selected which is capable to bring down the pH of alkaline textile wastewater in a short period of about two hours.

In another embodiment of the invention, the selected bacterium is cultured under defined conditions by using the bacterial carbonate medium followed by incubation at 37° C./120 rpm 8 hours for neutralizing the alkaline textile industrial wastewater.

In another embodiment of the invention, the grown culture is centrifuged at 5000–7000 rpm at 1–4° C. after attaining the heavy growth O.D (1.5).

In another embodiment of the invention, the bacterial pellet is dissolved in phosphate buffer (pH 6.8).

In another embodiment of the invention, neutralization of highly alkaline wastewater of textile industry is done by adding the bacterial pellet in 200 ml wastewater, wherein the lowering of pH from 12.0–11.5 to 7.5–7.00 was observed in 2 hr to 1.5 hr when checked by pH meter.

In another embodiment of the invention, the-bacterium, *Kurthia* sp. is used as a whole cell.

DETAILED DESCRIPTION OF THE INVENTION

The present invention provides a bacterial isolate and process of preparation of bacterial isolate *Kurthia* sp, (MTCC 5181) deposited at International Depository at IMTECH, Sector 39A, Chandigarh, India recognized by Budapest Treaty. The bacterial isolate, *Kurthia* sp, (MTCC 5181) is capable of neutralizing the highly alkaline wastewater of textile industry.

The bacterial isolate is capable of growth in a medium of pH range of 10.00–12.00.

It has been observed that the bacterial isolate is capable of lowering the pH (12.0 to 11.5) of textile industrial wastewater to neutral pH (7.5 to 7.00) within a short period (about two hour). The isolate is used in the form of a bacterial pellet to neutralize high pH (12.0 to 11.5) of textile industrial wastewater to neutral pH (7.5 to 7.0) in ratio ranging from 1:5 to 1:10.

The bacterial isolate is isolated from soil accumulated in a pipe of an effluent treatment plant of textile industry located in Chandigarh, India, through which alkaline wastewater has been passed over a period of long time. The bacterial isolate *Kurthia* sp is Gram-Positive, motile, catalase positive, and capable of reducing nitrate and hydrolyzing starch.

The process for preparing the bacterial isolate of bacterium *Kurthia* sp, (MTCC 5181) comprises:

(a) enriching soil contaminated with bacteria by providing a soil extract in basal carbonate medium for a period of 72–96 tours at 100–120 rpm at 35–37° C. in ratio ranges between 1:1–1:2;

(b) culturing the bacteria by using the basal carbonate medium at pH 1.5–12.00 and at 35–37° C. for 8–10 hours;

(c) Isolating the said bacteria by centrifuging the culture obtained from step (b) after attaining the heavy growth (O.D. 1.5–2.0) to obtain a pellet of bacterial cell;

(d) dissolving the pellet obtained from step (c) in phosphate buffer;

(e) neutralizing alkaline waste water (pH-12.00 to 11.5) of textile industry by adding the bacterial pellet obtained from step (d) in wastewater.

The contaminated soil is obtained from a pipe of an effluent treatment plant of textile industry located in Chandigarh, India. Enrichment of the soil from said site is done by taking 5–7 g of fresh soil in an autoclaved flask containing 100–110 ml soil extract, 50 µl Candid B (anti-fungal) and basal carbonate medium.

The soil extract is prepared by centrifuging the sterilized soil mixture at about 4000 rpm for about 20 min. The sterilized soil mixture is prepared by dissolving the dried soil in distilled water in ratio about 1:3 and autoclaved it at about 15 psi for about one hour.

The basal carbonate medium contains glucose, bacto-peptone, yeast extract, $K_2HPO_4.3H_2O$, $MgSO_4.7H_2O$ and sodium carbonate in ratio about 1:0.5:0.5:0.13:0.02:10 by W/V. A mixture of soil extract and basal carbonate medium is used to entrap the maximum bacterial flora of the site. The ratio between the said soil extract and the said basal carbonate medium is between 1:1–1:2.

The isolated bacterial isolates are cultured under defined conditions such as media, temperature, pH, carbon source etc. All the bacterial isolates (total three) are checked for their neutralizing capability to lower the pH of textile wastewater in a short period of time. Decrease in pH is monitored by pH meter. The bacterium is selected based on its capability of lowering the pH of alkaline textile wastewater in a short period of about two hours.

The selected bacterium is cultured under defined conditions by using the bacterial carbonate medium followed by incubation at 37° C./120 rpm 8 hours for neutralizing the alkaline textile industrial wastewater. The grown culture is centrifuged at 5000–7000 rpm at 1–4° C. after attaining the heavy growth O.D. (1.5). The bacterial pellet is dissolved in phosphate buffer (pH 6.8).

Neutralization of highly alkaline wastewater of textile industry is done by adding the bacterial pellet in 200 ml wastewater, lowering of pH from 12.0–11.5 to 7.5–7.00 was observed in 2 hr to 1.5 hr as checked by pH meter.

If desired, the bacterium, *Kurthia* sp. is used as a whole cell.

The bacterial strain concerned with the present invention is deposited at International Depository at IMTECH, Sector 39A, Chandigarh India recognized by Budapest Treaty.

| S. No. | Culture | MTCC ID No. |
|---|---|---|
| 1. | *Kurthia* sp. | (MTCC 5181) |

The above-mentioned bacterial strain exhibits a remarkable capability to neutralize highly alkaline textile industrial wastewater within a short period of 1.5–2 hours under defined conditions. The bacterial strain in the present invention has been isolated from the soil accumulated in the pipe of effluent treatment plant of textile industry located in Chandigarh, India, through which textile industrial wastewater has been passed over a period of long time. To isolate a potential bacterial isolate, 100–110 ml soil extract; 100–110 ml basal carbonate medium and 50 µl Candid B (antifungal). Basal carbonate medium containing 1% (w/v) glucose, 0.5% bacto-peptone, 0.5% yeast extact, 0.13% $K_2HPO_4.3H_2O$, and 0.02% $MgSO_4.7H_2O$. Sodium carbonate (10%) was sterilized separately and added to obtain a 1% concentration with initial pH of 10.5 in the medium. The enrichment flask was kept at 100–120 rpm for about 72 . 96 hours at 35–37° C.

For the preparation of soil extract, 1 Kg soil was taken and dried at 50° C. for 2 hours. 400 g of dried soil was dissolved in 960 ml single distilled water and autoclaved at 15 lbs for 1 hour. After autoclaving, the sample was centrifuged at 5000 rpm for 10 minlutes. The supernatant (extract) was collected and stored in sterile bottle for the preparation of enrichment flask and further use.

The enriched soil sample was serially diluted in 0.85% saline. 10µ from each respective dilution was spread onto agar petri plates containing soil extract and 50% basal carbonate medium. Basal carbonate medium containing 1% (w/v) glucose, 0.5% bacto-peptone, 0.5% yeast extract, 0.13% $K_2HPO_4.3H_2O$, and 0.02% $MgSO_4.7H_2O$. Sodium carbonate (10%) was sterilized separately and added to obtain a 1% concentration with initial pH of 10.5 in the medium. The plates thus obtained were incubated at 37±2° C. for 24–96 hrs in inverted position.

On the basis of colony morphology and color, total 3 bacterial isolates were selected to check their capability for neutraiing the alkaline wastewater. The single isolated colonies were picked and streaked on fresh plates containing the same medium. The above step was repeated till pure colonies were obtained.

To check the neutralizing capability of the three isolated bacteria, 200 ml textile industrial wastewater of high pH (12.0–11.5) was taken in glass flask at three places and each bacterial growth was added individually. Decrease in pH was monitored by a pH meter.

Out of three, only one isolate was found capable to grow on high pH (12.0–11.5) and bring down the pH of wastewater within a short period of 1.5–2 hours. This bacterium was designated as *Kurthia* sp and the main characteristic features are:

Bacterium, *Kurthia* sp, is aerobic in nature, is gram positive, shows optimal growth at a temperature in the range of 25–42° C., is capable of growth in a high pH environment (pH 12.00), is capable of hydrolyzing starch, is motile, catalase positive and reduces nitrate.

In a neutralization experiment, textile industrial wastewater was taken from a local textile industry. The bacterium *Kurthia* sp., as screened above, was inoculated in 200–220 ml basal carbonate medium. The culture was incubated at 35–37° C. for 8 hours under shaking conditions (100–120 rpm). After observing the heavy bacterial growth (Optical Density (O.D=1.5), the culture was centrifuged at 5000–7,000 rpm at about 1–4° C. The culture pellet was dissolved in about 20 ml phosphate buffer according to the size of pellet. This pellet was added in a flask containing 200 ml textile industrial waste water (pH 12.0–11.5)). The flask was kept at shaking conditions (100–120 rpm). Decrease in pH was observed after 1.5–2 hours. This bacterium, *Kurthia* sp, (MTCC 5181) has been capable to bring down the pH from 12–11.5 to 7.5–7 within a short period of 1.5–2 hours pH was monitored by a pH meter.

The invention further provides a process for the preparation of bacterial growth useful in neutralizing the alkaline wastewater:

a) Enriching the soil of the said site using soil extract and basal carbonate medium to isolate the bacteria having neutralization capability;

b) using the mixture of soil extract and basal carbonate medium containing about 1% (w/v) glucose, about 0.5% bacto-peptone, about 0.5% yeast extract, about 0.13% $K_2HPO_4.3H_2O$, and about 0.02% $MgSO_4.7H_2O$. Sodium carbonate (about 10%) was sterilized separately and added to obtain a 1% concentration with initial pH of 10.5 to entrap the desired potential bacteria from the said site;

c) culturing the said bacteria isolated from specific site under defined conditions such as media, temperature, pH, carbon source etc.;

d) checking the neutralizing capability of isolated bacterial isolates by inoculating them in 200–220 ml alkaline textile industrial waste water;

e) Decrease in pH was monitored by a pH meter;

f) selecting the bacterial isolate which can neutralize the alkaline waste water in a short period of time;

g) Culturing selected bacterium under defined conditions for neutralizing alkaline textile industrial wastewater. Basal carbonate medium was used to grow a culture. Culture flask was incubated at 35–37° C. for 8 hours at 100–120 rpm in order to obtain heavy growth;

h) centrifuging the resulting culture after attain the heavy growth O.D. (1.5);

i) collecting the bacterial pellet and dissolving in phosphate buffer;

j) Neutralizing the highly alkaline wastewater of textile industry by adding the bacterial pellet in 200 ml wastewater. Lowering of pH from 12.0–11.5 to 7.5–7.00 was observed in 1.5–2 hrs as checked by pH meter.

The following examples are given by way of illustration and therefore should not be construed to limit the scope of the present invention.

EXAMPLE 1

In an endeavor of exploring alkaliphilic bacteria, strategic isolation was done to entrap potential bacterial flora from soil accumulated in a pipe of an effluent treatment plant of textile industry located in Chandigarh, India through which alkaline waste water has been passed over a period of long time. Accumulated soil was collected from the said pipe to isolate the bacteria.

To isolate a potential bacterial isolate, 5 g soil from the said site was added in the 500 ml autoclaved flask containing 100 ml soil extract; 100 ml basal carbonate medium and 50 μl Candid B (antifungal). Basal carbonate medium containing 1% (w/v) glucose, 0.5% bacto-peptone, 0.5% yeast extract, 0.13% $K_2HPO_4.3H_2O$, and 0.02% $MgSO_4.7H_2O$. Sodium carbonate (10%) was sterilized separately and added to obtain a 1% concentration with initial pH of 10.5 in the medium. The enrichment flask was kept at 120 rpm for 96 hours at 37° C.

For the preparation of soil extact 1 Kg soil was taken and dried at 50° C. for 2 hours. 400 g of dried soil was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

The enriched soil sample was serially diluted in 0.85% saline. 100 ul from each respective dilution was spread onto agar petri plates containing soil extract and 50% basal carbonate medium. Basal carbonate medium containing 1% (w/v) glucose, 0.5% bacto-peptone, 0.5% yeast extract, 0.13% $K_2HPO_4.3H_2O$, and 0.02% $MgSO_4.7H_2O$. Sodium carbonate (10%) was sterilized separately and added to obtain a 1% concentration with initial pH of 10.5 in the medium. The plates thus obtained were incubated at 37±2° C. for 24–96 hrs in inverted position.

On the basis of colony morphology and color, total 3 bacterial isolates were selected to check their capability fbr neutraling the alkaline wastewater. The single isolated colonies were picked and streaked on fresh plates containing the same medium. The above step was repeated till pure colonies were obtained.

EXAMPLE 2

In order to explore the potential bacteria for neutralization of alkaline textile industrial wastewater, total three bacteria were isolated from the pipe through which textile industrial wastewater has been passed over a period of long time. These bacterial isolates were selected to check their capability for neutralizing the alkaline waste water. The single isolated colonies were picked and streaked on fresh agar plates containing the same medium. The above step was repeated till pure bacterial colonies were obtained.

To check the neutralizing capability of the three isolated bacteria, 200 ml textile industrial wastewater of high pH (12.00) was taken in 500 ml glass flask at three places and each bacterial growth was added individually. Decrease in pH was monitored by a pH meter (Table 1).

TABLE 1 pH reduction of alkaline wastewater by isolated alkaliphilic bacteria.

| Bacterial Isolates | Reduction in pH of waste water during course of time | | | | | | |
|---|---|---|---|---|---|---|---|
| | 0 hr | 0.5 hr | 1.0 hr | 1.5 hr | 2.0 hr | 2.5 hr | 3.0 hr |
| Isolate 1 | 12.12 | 12.11 | 12.11 | 12.10 | 12.10 | 12.01 | 12.00 |
| Isolate 2 | 12.12 | 9.24 | 8.05 | 7.67 | 7.04 | 7.03 | 7.01 |
| Isolate 3 | 12.12 | 12.10 | 12.4 | 11.98 | 11.86 | 11.77 | 11.70 |

EXAMPLE 3

On the basis of colony morphology and color, total 3 bacterial isolates were selected to check their capability for neutralizing the alkaline wastewater. The single isolated colonies were picked and streaked on fresh plates containing the same medium. The above step was repeated till pure colonies were obtained.

Out of three, only one isolate (Isolate 2), *Kurthia* sp, was found capable to grow on high pH (12.00) and bring down the pH (7.04) of wastewater within a short period of 2 hours. This bacterium was designated as *Kurthia* sp and the main characteristic features are:

(a) aerobic in nature
(b) gram positive
(c) shows optimum growth between 25–42° C.
(d) capable to grow in a high pH environment (pH 12.00)
(e) capable of hydrolyzing the starch
(f) is motile
(g) is catalase positive
(h) reduces nitrate.

EXAMPLE 4

In order to observe the growth of screened bacterium *Kurthia* sp on a suitable medium, two loops from agar plate of *Kurthia* sp were streaked onto plates of Nutrient broth medium and Basal carbonate medium. Basal carbonate medium containing 1% (w/v) glucose, 0.5% bacto-peptone, 0.5% yeast extract, 0.13% $K_2HPO_4.3H_2O$, and 0.02% $MgSO_4.7H_2O$. Sodium carbonate (10%) was sterilied separately and added to obtain a 1% concentration with initial ph of 10.5 in the medium. The plates thus obtained were incubated at 37±2° C. for 24–96 hrs in inverted position.

NB medium containing 2% agar was having original pH about 7 while BCM medium was having orual pH 10.5. For increasing the pH of media, Tris-HCL and $Na_2CO_3$—$NaHCO_3$ buffer were used.

| pH values | NB medium | BCM medium |
|---|---|---|
| 7.00 | + | + |
| 8.00 | + | ++ |
| 9.00 | ++ | +++ |
| 10.00 | – | ++++ |
| 11.00 | – | ++++ |
| 12.00 | – | +++++ |

+ Very poor growth
++ Poor growth
+++ Good growth
++++ Very good growth

It was observed that BCM medium of high pH is a suitable medium to grow the *Kurthia* sp.

EXAMPLE 5

Neutralization of alkaline textile wastewater was also done with lyophilized powder of *Kurthia* sp. Bacterial pellet of 40 ml culture (O.D.=1.5) was lyophilized and added to 500 ml flask containing 200 ml alkaline textile wastewater. Inoculated flask was kept at 37° C. for 2 hr. Decrease in pH was observed within two hours (Table 3). The experiment was done in duplicate (Set 1 and Set 2)

TABLE 3 pH reduction of alkaline wastewater by lyophilized bacterial powder of *Kurthia* sp.

| Bacterial Isolate | Reduction in pH of waste water during course of time | | | | | | |
|---|---|---|---|---|---|---|---|
| | 0 hr | 0.5 hr | 1.0 hr | 1.5 hr | 2.0 hr | 2.5 hr | 3.0 hr |
| *Kurthia* sp. (Set 1) | 12.11 | 9.56 | 8.22 | 7.45 | 7.23 | 7.02 | 7.01 |
| *Kurthia* sp (Set 2) | 12.11 | 9.33 | 8.35 | 7.67 | 7.12 | 7.03 | 7.00 |

ADVANTAGES

1. The neutralization of alkaline textile wastewater up *Kurthia* sp is an economical and effective process. In conventional acid-neutralization process, tones of acid are used for the neutralization while in the developed biological process decrease the cost drastically.
2. The neutralization of alkaline textile wastewater by biological mean is quite safe process as the utilization of acid in large quantities for the neutralization of wastewaters is not safe for the industry as the strong acid has dangerous effect on the health of workers as well as on the industrial processes. Besides this, use of large quantity of acid also increases the volume of industrial wastewaters to be drained out in the main stream.

We claim:

1. A biologically pure isolate, *Kurthia* sp, (MTCC 5181) deposited at International Depository at IMTECH, Sector 39A, Chandigarh, India recognized by Budapest Treaty.

2. An isolate as claimed in claim 1 wherein the isolate is capable of growth in a medium of pH range of 10–12.

3. An isolate as claimed in claim 1 wherein the isolate is capable of lowering pH of textile industrial wastewater having a pH of 11.5 to 12 to a pH of 7 to 7.5 within a period of about two hours.

4. An isolate as claimed in claim 1 wherein the isolate is capable of lowering pH of textile industrial wastewater having a pH of 11.5 to 12 to a pH 7 to 7.5 when used in a ratio ranging from 1:5 to 1:10 of isolate to wastewater.

5. An isolate as claimed in claim 1 wherein the isolate is isolated from soil accumulated in a pipe of an effluent treatment plant of textile industry located in Chandigarh, India, through which alkaline wastewater has passed.

6. An isolate as claimed in claim 1 wherein the isolate *Kurthia* sp is Gram-Positive, motile, catalase positive, and capable of reducing nitrate and hydrolyzing starch.

7. A process of preparing the biologically pure isolate of claim 1, comprising the steps of:
(a) extracting soil contaminated with bacteria suspected of comprising *Kurthia* sp;
(b) culturing the bacteria suspected of comprising the *Kurthia* sp in a mixture comprising the soil extracted in step (a), sterilized soil and basal carbonate medium;
(c) assaying the culture obtained in step (b) for a bacterial colony consisting of *Kurthia* sp: and
(d) if a bacterial colony consisting of *Kurthia* sp is found in the assaying step, isolating the bacterial colony from the culture to obtain the biologically pure isolate.

8. A process as claimed in claim 7 wherein step (b) is carried out for a period of 72–96 hours with centrifugation at 100–120 rpm and at a temperature in the range of 35–37° C.

9. A process as claimed in claim 7 wherein the ratio of sterilized soil to basal carbonate medium is in a range of 1:1–1:2.

10. A process as claimed in claim 7 wherein the bacteria is cultured in step (b) at a pH in a range of 1.5–12 and at a temperature in a range of 35–37° C. for 8–10 hours.

11. A process as claimed in claim 7 wherein the bacterial colony is isolated in step (d) by centrifugation after attaining heavy growth determined by measuring optical density till the optical density reaches the range of 1.5–2.0.

12. A process as claimed in claim 7 wherein the soil is extracted from a pipe of an effluent treatment plant of textile industry located in Chandigarh, India.

13. A process as claimed in claim 7 wherein the mixture in step (b) comprises 5–7 g of fresh soil, 100–110 ml of the sterilized soil, 50 µl of an anti-fungal substance and basal carbonate medium.

14. A process as claimed in claim 7 wherein the sterilized soil is prepared by centrifuging a sterilized soil mixture at about 4000 rpm for about 20 minutes.

15. A process as claimed in claim 14 wherein the sterilized soil mixture is prepared by mixing dried soil in distilled water in a ratio of about 1:3 and autoclaving the mixture at about 15 psi for about one hour.

16. A process as claimed in claim 7 wherein the basal carbonate medium contains glucose, bacto-peptone, yeast extract, $K_2HPO_4.3H_2O$, $MgSO_4.7H_2O$ and sodium carbonate in a ratio of about 1:0.5:0.5:0.13:0.02:10 by W/V.

17. A process as claimed in claim 7 wherein the culturing is performed under defined conditions of media, temperature, pH, and carbon source.

18. A process as claimed in claim 7 wherein the culture obtained in step (b) is centrifuged at 5000–7000 rpm at 1–4° C. after attaining heavy growth determined by an optical density of about 1.5.

19. A process as claimed in claim 7 wherein the bacterial colony isolated in step (d) is a bacterial pellet and the process further comprises dissolving the bacterial pellet in phosphate buffer having a pH of about 6.8.

20. A process for neutralizing alkaline wastewater having a pH of 11.5 to 12 comprising adding a cell pellet comprising the biologically pure isolate of claim 1 to the alkaline wastewater under conditions reduce pH of the alkaline waste water to a pH in the range of 7 to 7.5.

21. A process as claimed in claim 20 wherein the process comprises obtaining the biologically pure isolated by:
(a) extracting soil contaminated with bacteria suspected of comprising *Kurthia* sp;
(b) culturing the bacteria suspected of comprising the *Kurthia* sp in a mixture comprising the soil extracted in step (a), sterilized soil and basal carbonate medium;
(c) assaying the culture obtained in step (b) for a bacterial colony consisting of *Kurthia* sp; and (d) if a bacterial colony consisting of *Kurthia* sp is found in the assaying step, isolating the bacterial colony to obtain the biologically pure isolate.

22. A process as claimed in claim 21 wherein step (b) is carried out for a period of 72–96 hours with centrifugation at 100–120 rpm and at a temperature in the range of 35–37° C.

23. A process as claimed in claim 21 wherein the ratio of the sterilized soil to basal carbonate medium is in a range of 1:1–1:2.

24. A process as claimed in claim 21 wherein the bacteria is cultured in step (b) at a pH in a range of 1.5–12 and at a temperature in a range of 35–37° C. for 8–10 hours.

25. A process as claimed in claim 21 wherein the bacterial colony is isolated in step (d) by centrifugation after attaining heavy growth determined by measuring optical density till the optical density reaches a range of 1.5–2.0.

26. A process as claimed in claim 21 wherein the soil extracted in step (a) is from a pipe of an effluent treatment plant of textile industry located in Chandigarh, India.

27. A process as claimed in claim 21 wherein the mixture in step (b) comprises 5–7 g of extracted soil, 100–110 ml of the sterilized soil, 50 µl of an antifungal substance and basal carbonate medium.

28. A process as claimed in claim 21 wherein the sterilized soil is prepared by centrifuging a sterilized soil mixture at about 4000 rpm for about 20 minutes.

29. A process as claimed in claim 28 wherein the sterilized soil mixture is prepared by mixing the dried soil in distilled water in a ratio of about 1:3 and autoclaving the mixture at about 15 psi for about one hour.

30. A process as claimed in claim 21 wherein the basal carbonate medium contains glucose, bacto-peptone, yeast extract, $K_2HPO_4.3H_2O$, $MgSO_4.7H_2O$ and sodium carbonate in a ratio of about 1:0.5:0.5:0.13:0.02:10 by W/V.

31. A process as claimed in claim 21 wherein the culturing in step (b) is performed under defined conditions of media, temperature, pH, and carbon source.

32. A process as claimed in claim 21 wherein the culture obtained in step (b) is centrifuged at 5000–7000 rpm at 1–4° C. after attaining heavy growth determined by an optical density of about 1.5.

33. A process as claimed in claim 21 wherein the bacterial colony isolated in step (d) is a bacterial pellet and the process further comprises dissolving the bacteria pellet in phosphate buffer having a pH of about 6.8.

34. A process as claimed in claim 21 wherein the bacterial colony isolated in step (d) is checked for capability to lower pH of textile wastewater.

35. A process as claimed in claim 34, wherein a lowering in pH is monitored by a pH meter.

36. A process as claimed in claim 21 wherein the bacterial colony isolated in step (d) is cultured in a basal carbonate medium followed by incubation at 37° C. and centrifuged at 120 rpm for 8 hours.

37. A process as claimed in claim 20, wherein the cell pellet is added to 200 ml of the alkaline wastewater to lower pH from 11.5–12 to 7–7.5 over a period in the range of 1.5–2 hr measured by pH meter.

38. A process as claimed in claim 21 wherein the cell pellet is added in a ratio in a range of 1:5 to 1:10 to the alkaline wastewater.

39. A process as claimed in claim 21 wherein the bacterial isolate *Kurthia* sp is Gram-Positive, motile, catalase positive, and capable of reducing nitrate and hydrolysing starch.

* * * * *